US008779635B2

(12) United States Patent
Subrahmanyan et al.

(10) Patent No.: US 8,779,635 B2
(45) Date of Patent: Jul. 15, 2014

(54) ARRANGEMENT OF RETICLE POSITIONING DEVICE FOR ACTINIC INSPECTION OF EUV RETICLES

(71) Applicant: KLA-Tencor Corporation, Milpitas, CA (US)

(72) Inventors: Pradeep Subrahmanyan, Los Altos, CA (US); Mark Williams, Beaufort, SC (US); Samir Nayfeh, Shrewsbury, MA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/859,618

(22) Filed: Apr. 9, 2013

(65) Prior Publication Data

US 2013/0264494 A1 Oct. 10, 2013

Related U.S. Application Data

(60) Provisional application No. 61/622,269, filed on Apr. 10, 2012.

(51) Int. Cl.
*H02K 41/00* (2006.01)
*H02K 3/00* (2006.01)
(52) U.S. Cl.
USPC ............ 310/12.01; 310/12.05; 310/12.18; 310/12.19
(58) Field of Classification Search
CPC . G03F 7/70758; G03F 7/707; G03F 7/70708; G03F 7/70716
USPC ...................................... 310/12; 250/491, 492
See application file for complete search history.

(56) References Cited

U.S. PATENT DOCUMENTS

| | | | |
|---|---|---|---|
| 6,134,981 A | 10/2000 | Novak et al. | |
| 6,353,271 B1 * | 3/2002 | Williams | 310/12.06 |
| 7,459,808 B2 * | 12/2008 | Hol et al. | 310/12.06 |
| 7,728,462 B2 * | 6/2010 | Williams et al. | 310/12.14 |
| 8,279,399 B2 * | 10/2012 | Shibazaki | 355/53 |
| 2002/0089657 A1 | 7/2002 | Okubo | |
| 2003/0169409 A1 * | 9/2003 | Nishi | 355/51 |

(Continued)

OTHER PUBLICATIONS

Mochi, I., Goldberd, K.A., La Fontaine, B., Tchikoulaeva, A., and Holfeld, C.; "Actinic Imaging of Native and Programmed Defects on a Full-Field Mask", Proc. SPIE 7636, 76361A (2010).

(Continued)

*Primary Examiner* — Nikita Wells
*Assistant Examiner* — Johnnie L Smith
(74) *Attorney, Agent, or Firm* — Simpson & Simpson, PLLC (57) ABSTRACT

A reticle positioning apparatus for actinic EUV reticle inspection including a sealed inspection chamber containing a reticle stage for holding a reticle. The reticle stage has a magnetically suspended upper stage with a long travel in a "y" direction and a magnetically suspended lower stage with a long travel in an "x" direction; and a cable stage chamber isolated from the inspection chamber by a cable chamber wall. The cable stage chamber has a cable stage movable in the "y" direction; and a tube connected at one end to the reticle stage and to the cable stage at the other end. The tube passes from the cable stage through the inspection chamber through a seal in the chamber wall and opening into the cable entry chamber for entry of cables and hoses within the cable stage chamber, which cables and hoses pass through the tube to the reticle stage.

15 Claims, 6 Drawing Sheets

(56) References Cited

U.S. PATENT DOCUMENTS

| | | |
|---|---|---|
| 2009/0032708 A1 | 2/2009 | Nakasuji et al. |
| 2009/0128790 A1* | 5/2009 | Shibazaki ............. 355/53 |
| 2009/0225288 A1* | 9/2009 | Shibazaki ............. 355/30 |
| 2010/0066992 A1* | 3/2010 | Ono ...................... 355/72 |
| 2012/0281207 A1* | 11/2012 | Yoshimizu et al. ..... 356/237.5 |
| 2013/0183623 A1* | 7/2013 | Shibazaki ............. 430/296 |
| 2014/0049758 A1* | 2/2014 | Shibazaki ............. 355/30 |
| 2014/0049759 A1* | 2/2014 | Shibazaki ............. 355/30 |

OTHER PUBLICATIONS

LaPedus, Mark; "TSMC Says Actinic EUV Mask Inspection Lagging"; Sep. 22, 2011.

* cited by examiner

ARRANGEMENT OF RETICLE POSITIONING DEVICE FOR ACTINIC INSPECTION OF EUV RETICLES

CROSS REFERENCE TO RELATED APPLICATIONS

This claims priority from U.S. Provisional Application 61/622,269 filed Apr. 10, 2012; and from U.S. Non-Provisional patent application Ser. No. 13/859,618 filed Apr. 9, 2013.

BACKGROUND OF THE INVENTION

This invention generally relates to reticle inspection and more particularly relates to reticle stage design for actinic inspection of EUV reticles.

Reticles, i.e., photoreticles or photomasks, are transparent masks that allow electromagnetic radiation to pass in a defined pattern in a step in photolithography for preparation of integrated electronic circuits.

Over the years, component density has dramatically increased in integrated circuits until components can be measured in nanometers. The most recent commercial applications in photolithography employ very short wavelengths of radiation, e.g., EUV or extreme ultraviolet having wavelengths. "EUV" is an abbreviation for extreme ultraviolet light having wavelengths of less than 20 nm down to soft x-rays.

The extremely small size of components has led to extreme reticle requirements. Among problems encountered are issues with contamination. At such small sizes, contaminating particles in nanometer sizes can disrupt the integrity of the reticle and thus ruin resulting integrated circuits.

As a part of the preparation of such reticles, inspection is thus required. Unfortunately the inspection process itself can introduce contamination thus ruining or at least require cleaning to the reticle.

Thus one of the main requirements of a EUV photo-mask inspection is that no particles/contaminants are added to the photo-mask (reticle) during the inspection. Along with the exacting precision requirements demanded for inspecting EUV reticles, this places rather special requirements, especially on the reticle stage which forms the single largest moving component inside the chamber used for the inspection of the reticle.

Existing inspection apparatus has not met the demands of reticles formed using EUV since there exists too much probability that the inspection process will contaminate the reticle.

As an example, a current inspection apparatus includes an X stage and carries the reticle. The X stage rides on two Y stages that provide motion in both the Y and Z directions. The stages use pre-loaded air-bearings against mapped precision surfaces to constrain the other degrees of freedom and use interpolating encoders for feedback. Fine adjustments in the Y direction and auto-focus in the Z direction are provided by actuation/sensing built into the optical train.

The existing approach to positioning the reticle over the optics is limited in both precision and architecture and cannot be extended to the actinic inspection of EUVL reticles for the following reasons:

a. The design was created for use at atmospheric pressure and for a significantly less demanding contamination requirement that does not scale up to the requirements for EUV actinic inspection.

b. It uses air-bearings that would prove both a technical and economic challenge in being integrated into the vacuum chamber, and c. The architecture does not have either the resolution or precision to address the requirements posed by EUV mask inspection.

BRIEF SUMMARY OF THE INVENTION

In accordance with the invention a reticle positioning apparatus for actinic EUV reticle inspection is provided.

The reticle positioning apparatus includes:

a sealed inspection chamber containing a reticle stage for holding a reticle, said reticle stage having an upper stage with a long axis of travel in a "y" direction and a lower stage with a long axis of travel in an "x" direction; and a cable stage chamber isolated from the inspection chamber by a cable chamber wall, said cable chamber having a cable stage movable in the "y" direction, and a tube connected at a reticle stage end to the upper reticle stage and the cable stage at the other end, said tube passing from the cable stage chamber to the inspection chamber through a seal in the chamber wall and opening into the cable stage chamber for entry of cables and hoses within the cable stage chamber, which cables and hoses pass through the tube to the reticle stage. The tube is desirably flexibly connected to the reticle stage and flexibly connected to the cable stage.

The upper stage is preferably magnetically suspended by magnetic bearings in guides, in the inspection chamber.

The cable stage is slaved to the reticle stage such that movement of the upper stage in the "y" direction, at the location of the tube, is detected and provided to signal the cable stage to move the distance of movement of the upper stage in the y direction.

The lower stage is magnetically suspended by and slideable relative to guides on the upper stage.

The upper stage has a long travel direction along a reticle swathing direction y and the lower stage has a long travel along a loading and unloading direction y perpendicular to direction x.

The seal between the inspection chamber and the cable entry chamber may be any suitable seal known to those skilled in the art and preferably is an air-bearing feed through that is differentially pumped. The differentially pumped air bearing seal is one embodiment and could be replaced by a magnetic bearing or any other non-contact means of sealing two chambers.

Electromagnetic actuators are preferably used to move the cable and reticle stages. Reluctance actuators are preferably used to magnetically suspend the upper stage given the increased mass and Lorentzian actuators are used to magnetically suspend the lower stage given their linearity.

Short stroke actuators are also usually provided to move the reticle stages in additional degrees of freedom (other than the long travel axis) and for fine adjustment. In general sufficient actuators are provided to move both the upper and lower stages six degrees of freedom (DOF) each, leading to a total of twelve DOF for the reticle stage.

Desirably, electronic circuitry and firmware is provided for providing feedback linearization on the reluctance actuators and electronic circuitry is also desirably provided to send reference signals to the cable stage and reticle stage to ensure that the short stroke actuators do not saturate over desired ranges of motion.

The reticle positioning apparatus of claim 1 further preferably includes a metrology frame positioned on a projection optics box, which metrology frame serves as a reference for the reticle positioning apparatus with respect to the projection optics box.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DETAILED DESCRIPTION OF THE INVENTION

One of the main requirements of an EUV photo-mask inspection is that no particles/contaminants are added to the photo-mask (reticle) during the inspection. Along with the exacting precision requirements demanded for inspecting EUV reticles, this places rather special requirements, especially on the reticle stage which forms the single largest moving component inside the chamber used for the inspection of the reticle. An ameliorating fact is provided by the need for rather slow velocities and accelerations of the reticle stage. A stage design that combines best known methods for addressing both the contamination and precision requirements while taking advantage of the slow speed requirements is proposed. Key elements of the stage are the following:
  a. Upper Stage
  b. Lower Stage
  c. Stage Chamber
  d. Cable Stage
  e. Metrology Loop
  f. Control Algorithm The aforesaid elements are discussed in detail as follows.

Figure 1:
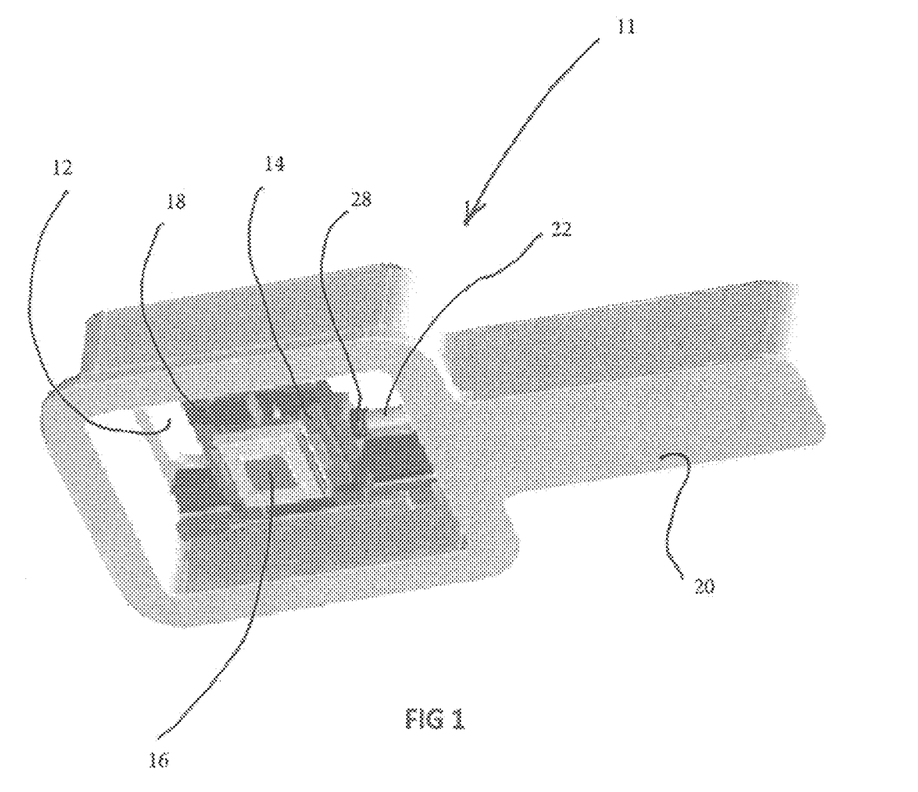
FIG. 1 shows a bottom perspective view of a reticle positioning apparatus of the invention with the inspection chamber open at the bottom to permit viewing of the inside of the chamber.
Figure 2:
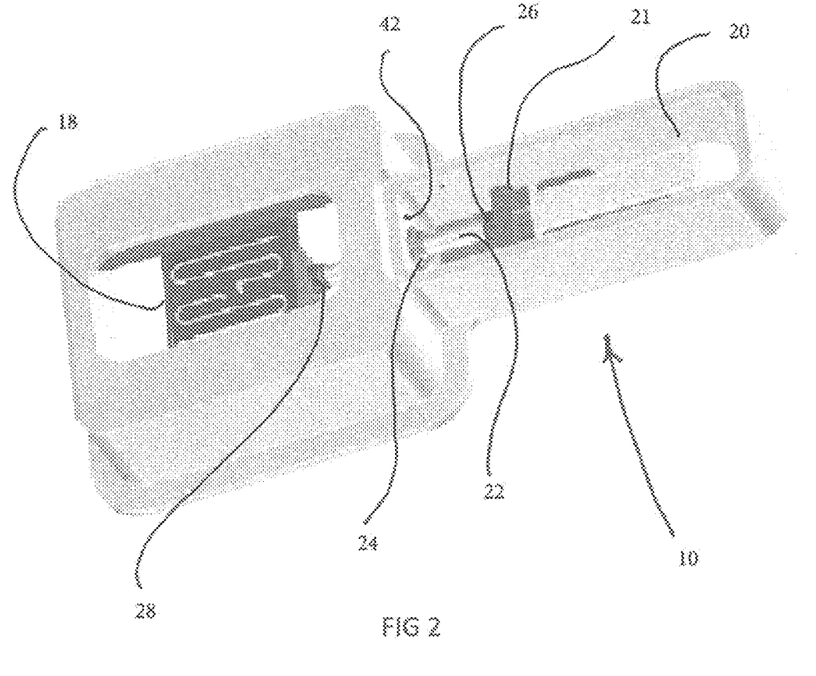
FIG. 2 shows a top perspective view of a reticle positioning apparatus of the invention with the top of the inspection chamber open to permit viewing of the inside of the inspection chamber.

FIGS. 1 and 2 illustrate an overall perspective of the reticle/cable stages proposed in this invention. The design seeks to minimize potential contamination sources inside the inspection chamber. This is done by adopting the following design features:

a. Use of a separate cable stage in a contained relatively "dirty" environment. One of the biggest contributors to particle generation is the presence of moving/flexing cables and hoses. Additionally, the interior of the inspection chamber has a hydrogen atmosphere which is deleterious to the materials traditionally used in the construction of such stages. The present invention has a cable stage that translates in the "y" direction and is loosely slaved to the reticle stage. All the cables and hoses required for providing power/cooling water to the stage elements are routed into a metal tube at the cable stages. The chamber containing the cable stage itself uses a nitrogen atmosphere to minimize adsorption of water onto the tube surface as it moves in and out of the inspection chamber (following the motion of the reticle stage itself). The tube is hinged appropriately both at the reticle stage and the cable stage to avoid unnecessary constraints. The "dirty" cable stage chamber and the "clean" inspection chamber are separated by an air-bearing feedthrough that is differentially pumped;

b. Use of magnetic bearings: The stage design uses magnetic bearings instead of fluid or rolling element bearings to avoid issues with contamination. In addition, it uses both reluctance and Lorentzian magnetic bearings. Specifically, reluctance bearings are used in the upper stage. They have the benefits of low current density requirement, higher stiffness, but suffer significantly from non-linearities and parasitic stiffness. As such, they are used in the upper stage to provide "gross" adjustments and prevent actuator saturation in the lower stage. Lorentz actuators are used in the lower stage—they have much higher current density requirements, require permanent magnets, run hotter and are not as stiff, but are nicely linear and are used primarily for "fine" motion control;

c. Use of separate motion stages: As described earlier, the motion of the reticle stage is split into two sets of 6 DOF (degree of freedom) stages. On each of the stages, provision is made for one long axis of travel and 5 short stroke DOF. Specifically, the lower X stage that uses Lorentz actuators for all its DOF has its long travel along the swathing (x) direction to provide a great deal of fidelity in this motion. The short stroke DOF are used for dynamic correction of errors during the swathing. The upper stage that uses reluctance actuators carries the mass of the lower stage and has its long travel along the loading/unloading (y) direction. The upper stage provides the gross corrections needed for the alignment of the reticle to the swathing direction, cable management and also serves as a reaction mass to the lower stage. A separate set of reaction masses is not used in this arrangement since the expected accelerations are fairly low and the mass ratio between the moving elements and the chamber itself is fairly small;

d. Metrology loop: A metrology frame is established on the projection optics box (described in the system level invention disclosure) and serves as the reference for the entire positioning system. A mirror made out of a zero CTE glass ceramic material forms the basis for the reticle chuck and is the target for six axis laser interferometry on the reticle stage;

e. Control Law and Implementation: The control law is devised to take advantage of the specific electromechanical characteristics of the design. Feedback linearization is utilized on the reluctance actuators, the upper stage is used as a reaction mass to the lower stage and filtered reference signals are sent to the stages to ensure that the short stroke actuators do not saturate over the ranges of motion desired.

Some advantages of the present invention are as follows:

a. Separation of the cable stage and the reticle stage and using a conduit to route hoses and cables between the two and a differentially pumped air bearing feedthrough to guide the conduit and separate the dirty and clean environments drastically minimizes the contamination risk posed to the reticle, the optics and the inspection chamber itself; and b. Removal of the requirement for reaction masses and dividing up the motions into two sets of 6 DOF stages allows for improved performance and significantly lower cost/footprint;

c. Alternate methods of construction involve using a combination of long and short stroke stages to provide 2 coarse/long DOF actuated outside the inspection chamber and other actuators to provide 6 fine DOF inside the chamber.

This approach allows the key driver—that of cable/hose management to minimize contamination to be satisfied. Cable management is performed outside the chamber for the long stroke stages and cables/hoses are passed to the short stroke stages in a very contained environment sealed using O-rings from the inspection chamber. However, all these approaches involve the use of an expensive slider that could potentially adsorb water as it travels back and forth across the clean and dirty environments. A much greater area exchange between the clean and dirty environments happens during the inspection and poses considerable risk, both technically and economically.

The apparatus of the invention may be described in more detail by reference to the drawings.

FIG. 1 shows a bottom perspective view of an embodiment of a reticle positioning apparatus for actinic EUV inspection 11 with an open bottom to permit internal viewing of the inspection chamber 12. The apparatus includes a sealed inspection chamber 12.

The reticle stage has an upper stage 18 and a lower stage 14. Stage 14, is for holding a reticle 16. Also visible in inspection chamber 12 is a tube 22 flexibly connected by reticle stage coupling 28 to upper stage 18.

FIG. 2 shows a top perspective view of the above embodiment open at the top to show contents. Cable stage 21 is visible, as is tube 22 and cable stage coupling 26. The inside of cable chamber 20 can be seen with air bearing feed through 24, cable stage coupling 26 and cable chamber wall 42. Upper stage 18 of reticle stage 11 along with flexible reticle stage coupling 28 are also visible.

Figure 3:
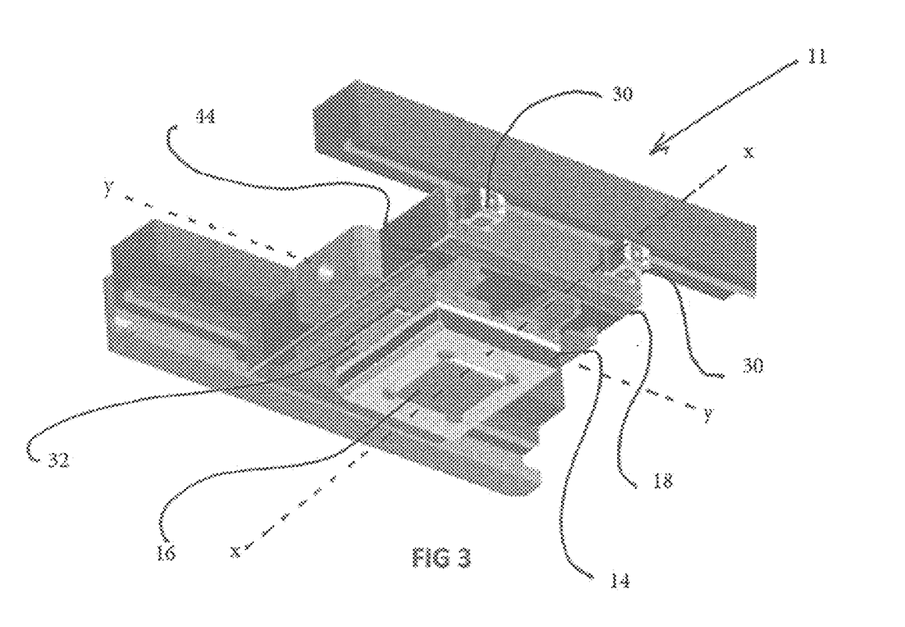
FIG. 3 shows a bottom view of the reticle stage assembly of the invention.

FIG. 3 shows a bottom view of reticle stage assembly 11. Reticle stage upper stage 18 and reticle stage lower stage 14 are clearly visible. It can be seen that reticle lower stage 14 slideably interacts with reticle stage 18 through reticle lower stage guides 44 and that reticle upper stage 18 interacts with reticle upper stage guides 46 secured to inspection chamber 12 by means of magnetic bearings 30. It can be see that reticle upper stage 18 moves in a long direction "y" and reticle lower stage 14 moves in a long direction "x".

Figure 4:
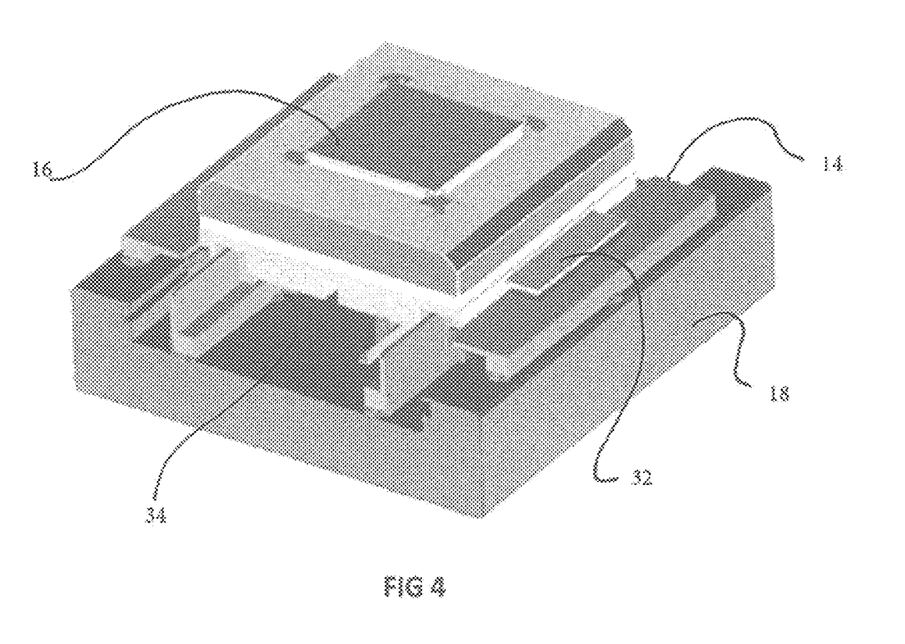
FIG. 4 shows a perspective view of the lower reticle stage assembly of the invention.

FIG. 4 shows a magnified perspective view of the relationship of reticle lower stage 14 with reticle upper stage 18, showing guides 44 and short stroke actuators 34.

Figure 5:
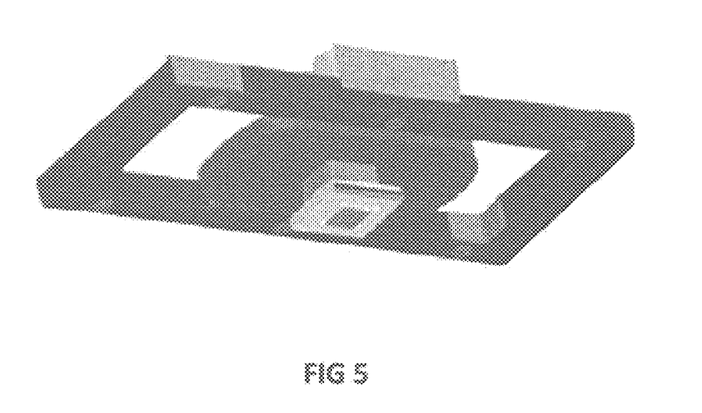
FIG. 5 shows a perspective view of an alternative embodiment of a 2 coarse/6 fine movement design of an inspection chamber with reaction masses.
Figure 6:
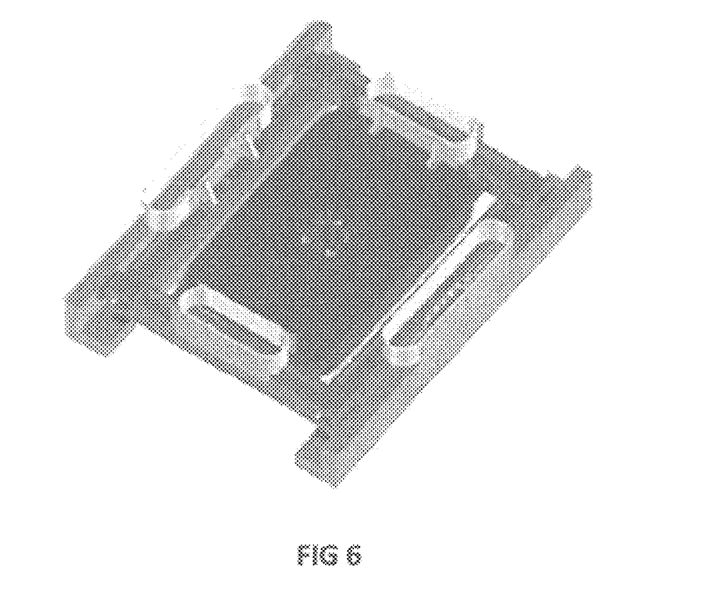
FIG. 6 shows a perspective view of an alternative embodiment of a 2 coarse/6 fine movement design of an inspection chamber without reaction masses.

FIGS. 5 and 6 show alternative embodiments as indicated in the Brief Description of the several views of the drawings.

Figure 7:
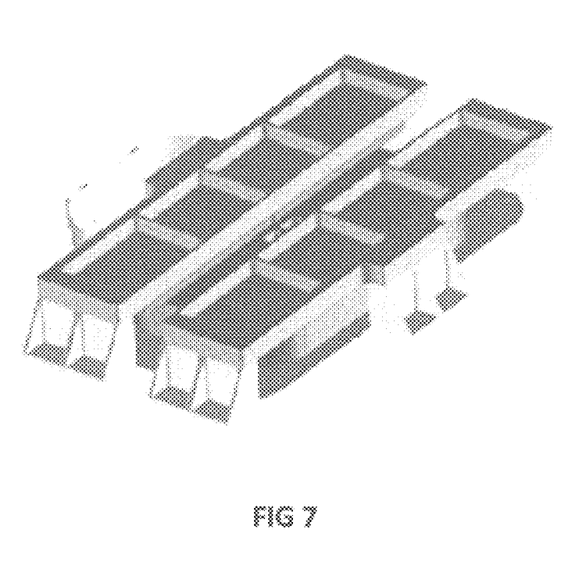
FIG. 7 shows a perspective view of planar motors for simplified movement.

FIG. 7 shows a perspective view of planar motors that may alternatively be used as actuators in accordance with the invention.

EUV light from a projection optics box is used for inspection. The optics box is provided with a metrology frame serving as a reference for the reticule positioning apparatus 10.

What is claimed is:

1. A reticle positioning apparatus for actinic EUV reticle inspection comprising:
    a sealed inspection chamber containing:
    a reticle stage for holding a reticle, said reticle stage having an upper stage with a long travel in a y direction and a lower stage with a long travel in an x direction; and
    a cable entry chamber isolated from the inspection chamber by a cable chamber wall, said cable entry chamber having a cable stage movable in the y direction, and
    a tube connected at a reticle stage end to the reticle stage and within the cable stage chamber to the cable stage, said tube passing from the cable stage through the inspection chamber through a seal in the chamber wall and opening into the cable stage chamber for entry of cables and hoses within the cable stage chamber, which cables and hoses pass through the tube to the reticle stage,
    said cable stage being slaved to the reticle stage such that movement of the upper stage in the y direction, at the location of the tube, is detected and provided to signal the cable stage to move the distance of movement of the upper stage in the y direction.

2. The reticle positioning apparatus of claim 1 wherein the lower stage is magnetically suspended by and slideable relative to guides on the upper stage.

3. The reticle positioning apparatus of claim 1 wherein the seal between the inspection chamber and the cable entry chamber comprises an air-bearing feed through that is differentially pumped.

4. The reticle positioning apparatus of claim 1 wherein the seal between the inspection chamber and the cable entry chamber comprises a magnetic seal bearing.

5. The reticle positioning apparatus of claim 1 wherein the seal provides a protection factor against both molecular and particulate contaminants generated by the motion of the cables in the cable stage chamber from entering the clean reticle stage (inspection) chamber.

6. The reticle positioning apparatus of claim 1 where the tube is flexibly connected to the reticle stage and flexibly connected to the cable stage.

7. The reticle positioning apparatus of claim 1 where the cable stage/feedthrough arrangement is mounted in such a way to attenuate disturbance forces from the motion of the cables from affecting the motion of the reticle stage during an inspection, thus avoiding image shifts and blurs during the inspection.

8. The reticle positioning apparatus of claim 1 wherein the upper stage is magnetically suspended in guides, in the inspection chamber, by magnetic bearings.

9. The reticle positioning apparatus of claim 6 wherein short stroke actuators are provided to move both the upper and lower the reticle stages in additional degrees of freedom and for fine adjustment.

10. The reticle positioning device of claim 1 wherein reluctance and Lorentzian actuators are used.

11. The reticle positioning apparatus of claim 8 wherein the upper stage serves as a partial balance mass for the lower stage for the accelerations expected during inspection.

12. The reticle positioning apparatus of claim 1 wherein the upper stage has a long travel direction along a reticle swathing direction x and the reticle stage has a long travel along a loading and unloading direction y perpendicular to direction x.

13. The reticle positioning apparatus of claim 8 wherein electronic circuitry and firmware is provided for providing feedback linearization on the reluctance actuators.

14. The reticle positioning apparatus of claim 8 wherein electronic circuitry and firmware is provided to send reference signals to the cable stage and reticle stage to ensure that the short stroke actuators do not saturate over desired ranges of motion.

15. The reticle positioning apparatus of claim 1 further comprising a metrology frame positioned on a projection optics box, which metrology frame serves as a reference for the reticle positioning apparatus.

* * * * *